US 9,492,206 B2

United States Patent
Black

(10) Patent No.: US 9,492,206 B2
(45) Date of Patent: *Nov. 15, 2016

(54) INTERSPINOUS LIGAMENT TRANSVERSE CONNECTOR

(71) Applicant: GLOBUS MEDICAL, INC., Audubon, PA (US)

(72) Inventor: Michael Black, Swarthmore, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/929,996

(22) Filed: Nov. 2, 2015

(65) Prior Publication Data

US 2016/0051291 A1    Feb. 25, 2016

Related U.S. Application Data

(63) Continuation of application No. 14/297,206, filed on Jun. 5, 2014, now Pat. No. 9,204,900, which is a continuation of application No. 13/181,062, filed on Jul. 12, 2011, now Pat. No. 8,777,996.

(60) Provisional application No. 61/363,387, filed on Jul. 12, 2010.

(51) Int. Cl.
  *A61B 17/56* (2006.01)
  *A61B 17/70* (2006.01)

(52) U.S. Cl.
  CPC ....... *A61B 17/7052* (2013.01); *A61B 17/7049* (2013.01)

(58) Field of Classification Search
  USPC ......................................................... 606/250
  See application file for complete search history.

(56) References Cited

U.S. PATENT DOCUMENTS

| | | | | |
|---|---|---|---|---|
| 5,569,246 A | * | 10/1996 | Ojima ................ | A61B 17/7049 606/250 |
| 7,699,873 B2 | * | 4/2010 | Stevenson .......... | A61B 17/7067 606/248 |
| 2006/0009766 A1 | * | 1/2006 | Lee .................... | A61B 17/7052 74/1 R |
| 2007/0049932 A1 | * | 3/2007 | Richelsoph .......... | A61B 17/645 606/252 |
| 2007/0233089 A1 | * | 10/2007 | DiPoto ............... | A61B 17/7011 606/279 |
| 2010/0204732 A1 | * | 8/2010 | Aschmann ......... | A61B 17/7062 606/249 |

* cited by examiner

*Primary Examiner* — Jan Christopher Merene

(57) ABSTRACT

An interspinous cross connector system configured and designed to be implanted through the interspinous ligament by a rod that can puncture through the ligament while leaving the ligament intact. The cross connector system includes a first and second elongate rod and a third elongate rod connecting the first and second elongate rods using a cross connection assembly. The cross connection assembly includes a one-piece L-shaped connecting body comprising a receptacle facing outwards towards the first rod and away from the second rod and a clamp, and a set screw selectively positioned to securely hold the connecting body to the first rod. The connecting body is disposed substantially between the first and second elongate rods. The clamp allows the connecting body to slidingly engage with the third rod.

18 Claims, 6 Drawing Sheets

INTERSPINOUS LIGAMENT TRANSVERSE CONNECTOR

CROSS-REFERENCE TO RELATED TO APPLICATIONS

This patent application is a Continuation of U.S. patent application Ser. No. 14/297,206 filed on Jun. 5, 2014, now U.S. Pat. No. 9,204,900, which is a Continuation of U.S. patent application Ser. No. 13/181,062 filed on Jul. 12, 2011, now U.S. Pat. No. 8,777,996, which claims priority to U.S. Provisional Application No. 61/363,387 filed on Jul. 12, 2010. The content and subject matter of these applications are hereby incorporated by reference in their entirety, including all text and figures, for all purposes.

FIELD OF THE INVENTION

The present invention relates to device which stabilizes the spine. In particular, the present invention is related to stabilizing the spine through the use of rods and rod connectors.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. Surgeons utilize polyaxial bone screws throughout the spine for posterior fusion. The rigidity or stiffness of posterior fusion systems is commonly augmented by the use of trans-connectors or t-connectors. The screw trajectory and placement is often dictated by the natural anatomy and frequently results in situations where the polyaxial bone screws are very close or even touch the adjacent screws.

In the abovementioned situation, a standard t-connector or trans-connector that affixes directly onto the titanium alloy rods may not be suitable due to the proximity of the bone screws. There is a need for a transverse connector which would be ideally suited to provide rigidity to the construct by puncturing through the interspinous ligament.

SUMMARY OF THE INVENTION

The present invention provides a method for stabilizing the spine including the steps for creating an access path to the posterior portion of the spine, positioning a first and second elongate rod longitudinally on opposing portions of the spine, piercing a portion of the interspinous ligament with a third elongate rod, and positioning the third elongate rod connecting the first and second elongated rods in a cross connection assembly. The cross connection assembly includes a one-piece connecting body comprising a receptacle facing outwards towards the first rod and away from the second rod and a clamp, and a set screw selectively positioned to securely hold the connecting body to the first rod. The connecting body is disposed substantially between the first and second elongate rods. The clamp allows the connecting body to slidingly engage with the third rod. A fastener causes the clamp to be clamped around the third rod, thereby locking the third rod relative to the connecting body. The third rod is configured and designed with frusto-conical tips for piercing the interspinous ligament.

BRIEF DESCRIPTION OF THE DRAWINGS

The attached drawings illustrate the elements of the present invention. Design and utility features of the present invention are also disclosed.

DETAILED DESCRIPTION OF THE INVENTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to limit the scope of the disclosure, including the claims, is limited to that embodiment.

The interspinous transverse connector is configured and designed to be implanted through the interspinous ligament by a rod that can puncture through the ligament, while at the same time leaving the ligament in tact. Generally, in spinal procedures for implanting trans-connectors systems, the interspinous ligament is removed and a traditional cross connector is positioned. However, there is no need to remove the interspinous ligament, therefore by positioning the present interspinous connector system, stabilizing the spine decreases operating time, and increases the speed of recovery and the bodies natural structures will continue to aid in stabilizing the spine.

Figure 1:
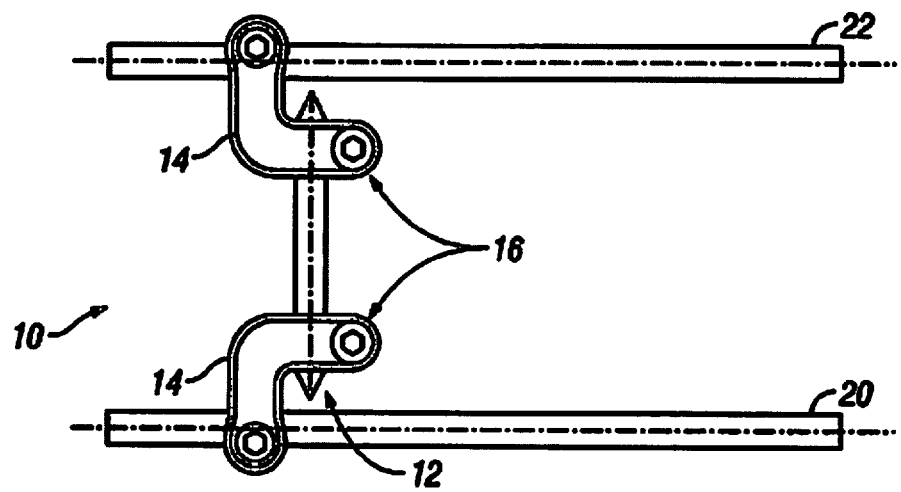
FIGS. 1-4 illustrate various views of one exemplary embodiment of a transverse connector system according to the present invention.
Figure 2:
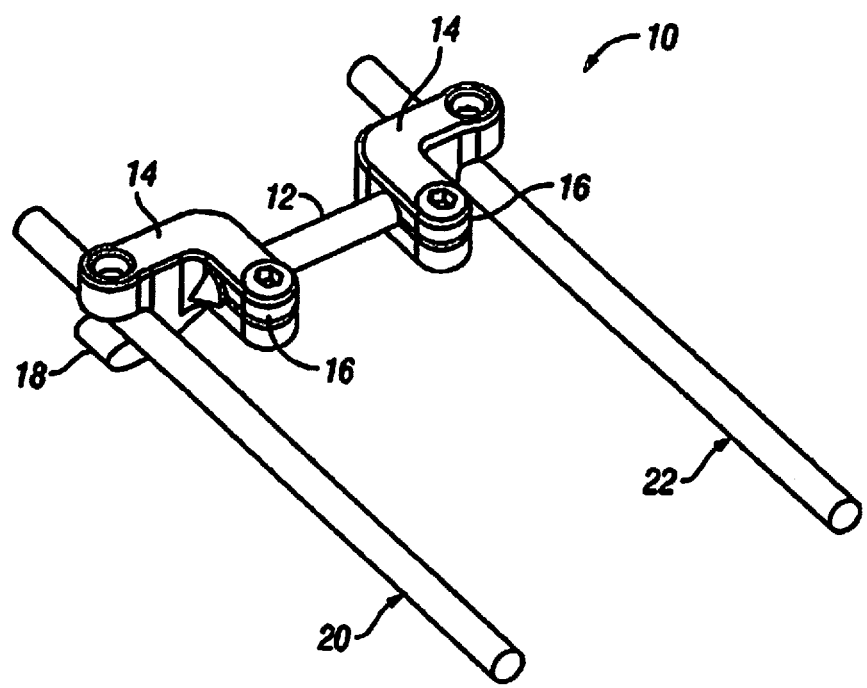
Figure 3:
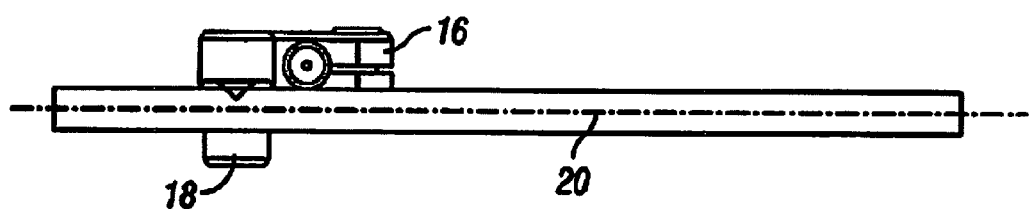
Figure 4:
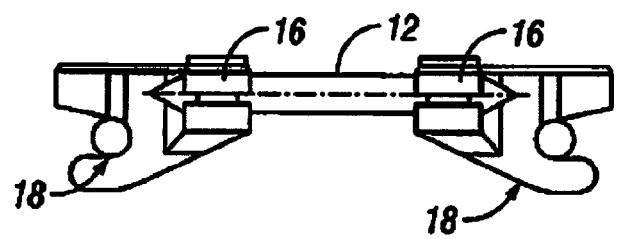

The first embodiment of the present invention, as illustrated in FIGS. 1-4 show a bullet-tipped or frusto-conical ends of a cross connector system 10 for puncturing through the interspinous ligament and enables the positioning of the cross connector 10 regardless of the orientation. The rod 12 is fixed to the body 14 of the connector 10 by a clamp 16 provided on opposite sides of the system. Each connector body 14 is provided with a hook 18 on the end for coupling to the posterior rods 20 and 22.

As illustrated in FIGS. 1-4, posterior rods 20 and 22 preferably run along the length of at least two or more vertebrae. Each rod 20 and 22 is preferably fixed to the vertebrae. In order to align the two or more vertebrae, rods 20 and 22 are preferably held in place using, for example, a fixation device. The present invention comprises, as mentioned above, two connecting bodies 14 that are preferably connected using a third rod, which allows the two rods 20 and 22 to be fixed in place relative to one another. Each of the connecting bodies preferably comprise an opening for passing the third rod that is capable of fixing the connecting body in place relative to the third rod using, for example, a screw. The opening preferably includes a c-ring having a spherical curvature, which may be placed within the opening to pass the third rod. The spherical curvature of the c-ring preferably prevents it from being forced out of the opening under normal conditions. The c-ring is capable of allowing the two connecting bodies to translate axially, or side to side, with respect to the third rod. This allows the spacing between the two rods 20 and 22 to be adjusted during, for example, an operation. Once the two connecting bodies are positioned as desired, they may be fixed in place relative to the third rod.

Figure 5:
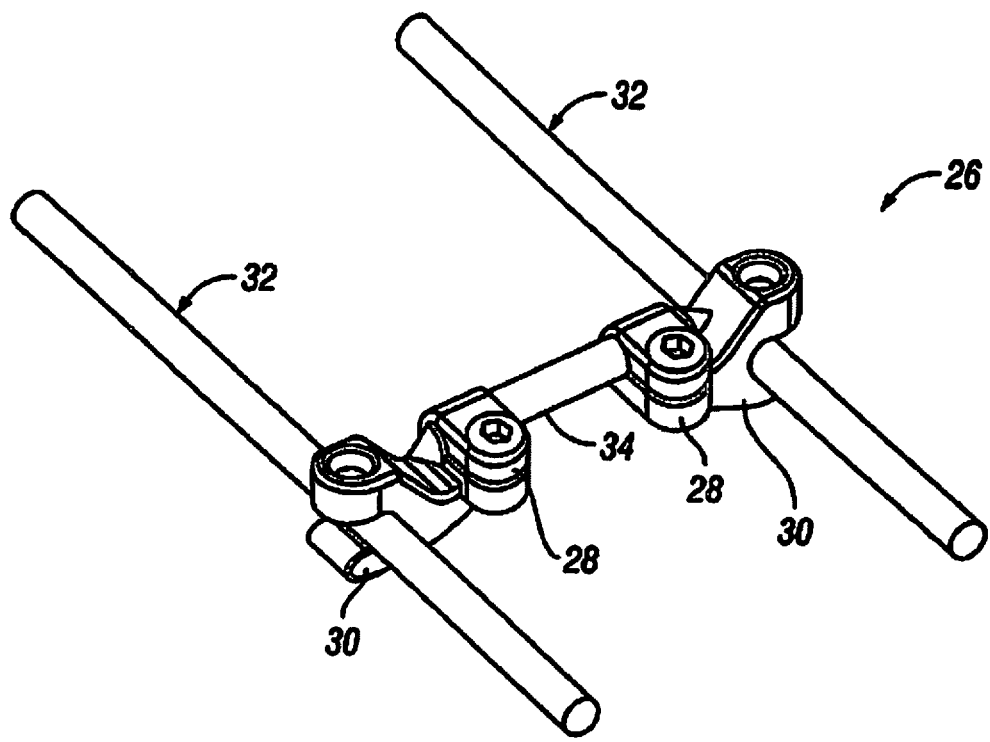
FIGS. 5-8 illustrate yet another embodiment of a transverse connector system according to the present invention.
Figure 6:
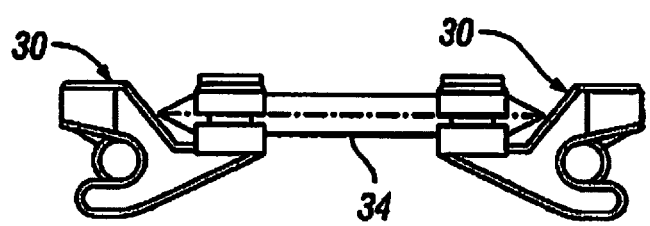
Figure 7:
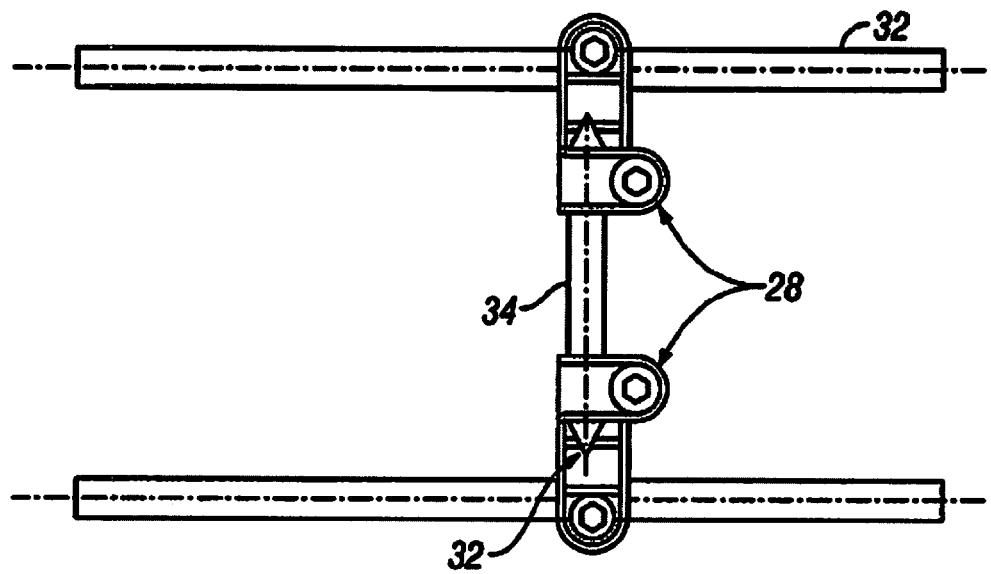
Figure 8:
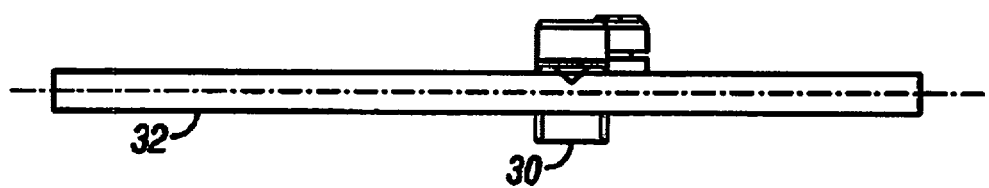

The second embodiment of the present invention, as illustrated in FIGS. 5-8, show a connector system 26 having multiple clamps 28 provided with hooks 30 capable of coupling to posterior rods 32. The cross connector rod 34 is configured to be in-line with the posterior hooks 30 of the clamps 28. The cross connector rod 34 is configured and designed with a frustoconical ends. The cross connector rod 34 is designed so that a surgeon can use the frustoconical ends to pierce the interspinous ligament rather than removing the interspinous ligament.

Figure 9:
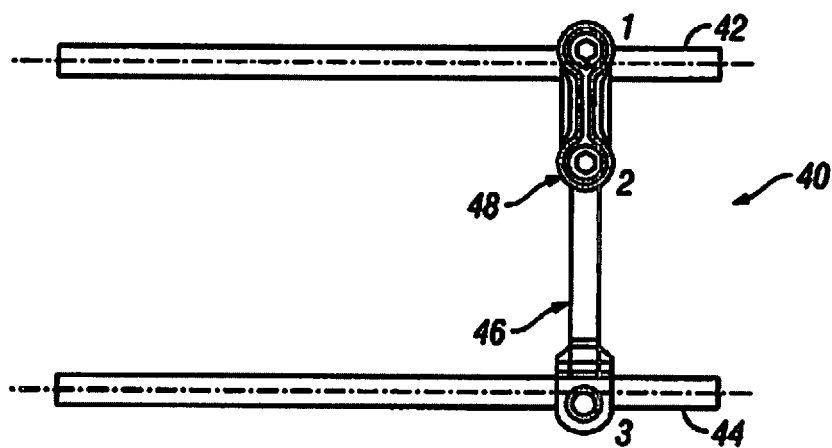
FIGS. 9-12 illustrate yet another embodiment of a transverse connector system according to the present invention.
Figure 10:
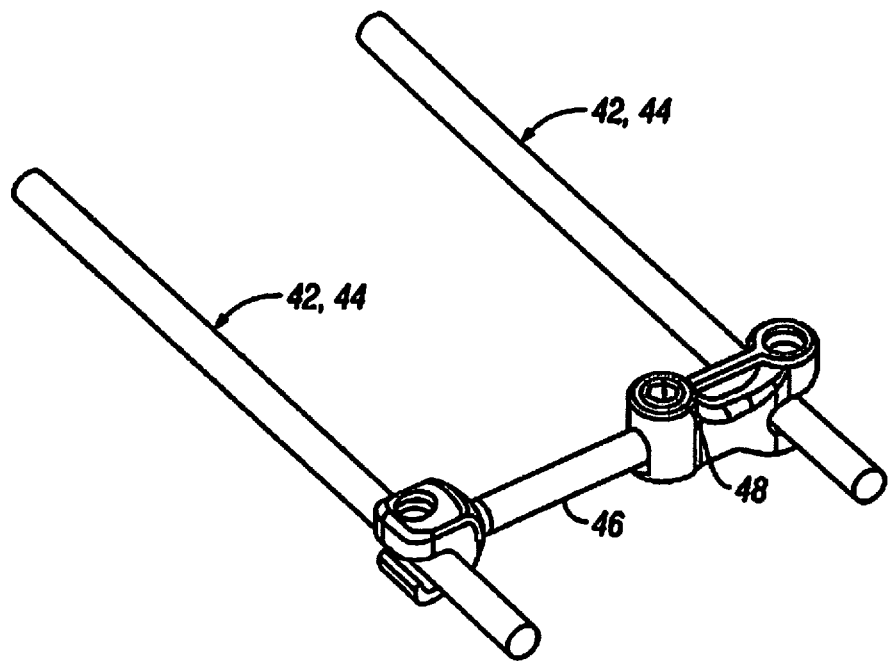
Figure 11:
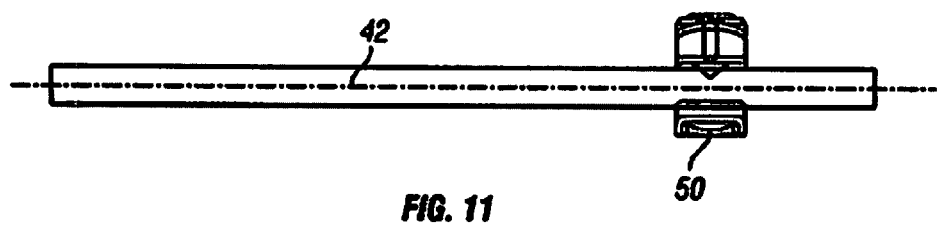
Figure 12:
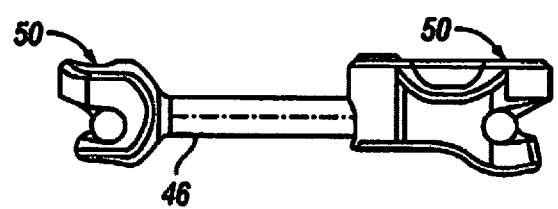

The third embodiment of the present invention, as illustrated in FIGS. 9-12, another inline cross connector system 40 attached to posterior rods 42 and 44. The cross connector 40 in the embodiment is integral to a first portion 46 of the hook end of the connector body of the construct and the locking point 48 for the cross connector is integral to the contra-lateral hook 50 and configured to be inline with the hook itself.

In the embodiments illustrated in FIGS. 1-8, the cross connecting rod is bullet shaped at the ends so that the ends may puncture through the interspinous ligament. In the embodiment illustrated in FIGS. 9-12, a single end of the cross connecting rod is bullet shaped and the other end is integral and/or coupled to the opposite hook portion of the connector assembly. Although the ends of the cross connector rod are bullet shaped, it should be noted that any shape that enables the cross connector rod to puncture through the interspinous ligament may be used. Additionally, it should be noted that the clamps in all the embodiments are tightened using a set screw to secure the rods into their proper position. Also, the hooks at the opposing ends of all the embodiments are also provided with a set screw to tighten down on the posterior rods.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

What is claimed is:

1. A cross connector system for stabilizing the spine comprising:
   a first elongate rod and a second elongate rod;
   a third elongate rod connecting the first and second elongate rods;
   a one-piece connecting body comprising a first elongated portion having first and second ends, a second elongated portion having first and second ends, wherein the first end of the first elongated portion comprises a receptacle facing outwards towards the first rod and away from the second rod and the second end of the second elongated portion comprises a clamp, the clamp comprising an upper clamp portion and a lower clamp portion and an opening therebetween;
   a first set screw selectively positioned to securely hold the connecting body to the first rod; and
   a second set screw selectively positioned to securely hold the connecting body to the third rod,
   wherein the second set screw is located at the second end of the second elongated portion and the first set screw is located at the first end of the first elongated portion,
   wherein when the first and second set screws are secured to the connecting body, the second set screw and first set screw are offset both vertically and horizontally along a plane that is perpendicular to a central longitudinal axis of one of the first set screw and second set screw,
   wherein the clamp allows the connecting body to slidingly engage with the third rod;
   wherein the second set screw causes the clamp to be clamped around the third rod, thereby locking the third rod relative to the connecting body, and
   wherein the third rod is configured and designed with frusto-conical tips configured for puncturing an interspinous ligament.

2. The system according to claim 1, wherein the connecting body is configured to rotate about a transverse axis.

3. The system according to claim 1, wherein the connecting body is configured to rotate about an axis perpendicular to a transverse axis.

4. The system according to claim 1, wherein the first elongate rod is positioned substantially parallel to the second elongate rod.

5. The system according to claim 1, wherein the third elongate rod is positioned substantially perpendicular to the first and second elongate rods.

6. The system according to claim 1, wherein the first end of the first elongated portion of the connecting body comprises a hook.

7. The system according to claim 1, wherein one of the frusto-conical tips of the third elongate rod extends beyond the second elongated portion of the connecting body.

8. The system according to claim 1 further comprising a second one-piece connecting body comprising a first elongated portion having first and second ends, a second elongated portion having first and second ends, wherein the first end of the first elongated portion comprises a receptacle facing outwards towards the second rod and away from the first rod and the second end of the second elongated portion comprises a clamp, the clamp comprising an upper clamp portion and a lower clamp portion and an opening therebetween.

9. A transverse fixation system for stabilizing the spine comprising:
   a first and a second elongate rod;
   a first and a second c-ring, each c-ring comprising an outer surface having a spherical curvature and first and second free ends facing each other to define an opening;
   a third elongate rod;
   a first and a second one-piece connecting body, the first and second one-piece connecting bodies each comprising a first elongated portion having first and second ends, a second elongated portion having first and second ends, wherein the first end of the first elongated portion comprises a receptacle facing outwards towards either the first rod or second rod and away from the other of the first rod or second rod, and the second end of the second elongated portion comprises a clamp, the clamp comprises an upper clamp portion and a lower clamp portion and an opening therebetween, wherein the clamp is disposed around either the first or the second c-ring and one end of the third elongate rod having a curved surface corresponding to the opening of the first or second c-ring;

a first fastener selectively positioned to securely hold the first connecting body to the first rod;

a second fastener selectively positioned to securely hold the second connecting body to the second rod;

a first set screw capable of securing the first clamp to the third rod;

wherein the first c-ring and first clamp allow the first connecting body to slidingly engage with the third elongate rod;

wherein rotation of the first set screw causes the first clamp to be clamped around the third elongate rod relative to the first connecting body;

a second set screw capable of securing the second clamp to the third rod;

wherein the first fastener is located at the first end of the first elongated portion of the first connecting body, the first set screw is located at the second end of the second elongated portion of the first connecting body, the second fastener is located at the first end of the second elongated portion of the second connecting body;

wherein the second c-ring and second clamp allow the second connecting body to slidingly engage with the third elongate rod; and wherein rotation of the second set screw causes the second clamp to be clamped around the third elongate rod relative to the second connecting body;

wherein the first and second c-ring comprise a notch selectively positioned on an inner face of the c-ring and substantially opposite the opening, wherein the third elongate rod is configured with a frusto-conical tip configured for piercing a portion of the interspinous ligament.

10. The system according to claim 9, wherein the first and second clamps hold the first and second connecting bodies in place relative to the third rod.

11. The system according to claim 9, wherein the first and second connecting bodies are configured to translate axially relative to the third rod.

12. A system for stabilizing the spine comprising:
a first and second elongate rod;
a third elongate rod connecting the first and second elongated rod in a cross connection assembly comprising:
a one-piece connecting body comprising a first elongated portion having first and second ends, a second elongated portion having first and second ends, the second end of the first elongated portion and the first end of the second elongated portion are integrally formed with each other, wherein at least a portion of the first end of the first elongated portion is substantially arcuate and comprises a receptacle facing outwards towards the first rod and away from the second rod, and the second end of the second elongated portion comprises a clamp, the clamp comprising an upper clamp portion and a lower clamp portion and an opening therebetween; and a set screw selectively positioned to securely hold the connecting body to the first rod;

wherein the connecting body is disposed substantially between the first and second elongate rods;

wherein the clamp allows the connecting body to slidingly engage with the third rod;

wherein a fastener causes the clamp to be clamped around the third rod, thereby locking the third rod relative to the connecting body, wherein the fastener is located at the second end of the second elongated potion and the set screw is located at the first end of the first elongated portion such that from a top view of the one-piece body, the set screw is offset both vertically and horizontally from the fastener;

wherein the third rod is configured and designed with frusto-conical tips.

13. The system according to claim 12, wherein the connecting body is configured to rotate about a transverse axis.

14. The system according to claim 12, wherein the connecting body is configured to rotate about an axis perpendicular to a transverse axis.

15. The system according to claim 12, wherein the first elongate rod is positioned substantially parallel to the second elongate rod.

16. The system according to claim 12, wherein the first end of the first elongated portion of the connecting body comprises a hook.

17. The system according to claim 12, wherein one of the frusto-conical tips of the third elongate rod extends beyond the second elongated portion of the connecting body.

18. The system according to claim 12 further comprising a second one-piece connecting body comprising a first elongated portion having first and second ends, a second elongated portion having first and second ends, the second end of the first elongated portion and the first end of the second elongated portion are integrally formed with each other to form an L-shaped body, wherein the first end of the first elongated portion comprises a receptacle facing outwards towards the second rod and away from the first rod and the second end of the second elongated portion comprises a clamp, the clamp comprising an upper clamp portion and a lower clamp portion and an opening therebetween.

* * * * *